United States Patent
Chen et al.

(10) Patent No.: US 11,708,363 B2
(45) Date of Patent: Jul. 25, 2023

(54) METHOD FOR PREPARING A KEY INTERMEDIATE FOR THE SYNTHESIS OF STATINS

(71) Applicant: Fudan University, Shanghai (CN)

(72) Inventors: Fener Chen, Shanghai (CN); Dang Cheng, Shanghai (CN); Minjie Liu, Shanghai (CN); Zedu Huang, Shanghai (CN); Yuan Tao, Shanghai (CN); Jiaqi Wang, Shanghai (CN)

(73) Assignee: Fudan University, Shanghai (CN)

( * ) Notice: Subject to any disclaimer, the term of this patent is extended or adjusted under 35 U.S.C. 154(b) by 23 days.

(21) Appl. No.: 17/488,276

(22) Filed: Sep. 28, 2021

(65) Prior Publication Data

US 2022/0017508 A1 Jan. 20, 2022

(30) Foreign Application Priority Data

Sep. 30, 2020 (CN) .......................... 202011064252.2

(51) Int. Cl.
 *C07D 417/12* (2006.01)
(52) U.S. Cl.
 CPC ................................. *C07D 417/12* (2013.01)
(58) Field of Classification Search
 CPC .................................................... C07D 417/12
 USPC ........................................................ 548/170
 See application file for complete search history.

(56) References Cited

U.S. PATENT DOCUMENTS

2012/0136151 A1   5/2012   Lee

FOREIGN PATENT DOCUMENTS

| | | | |
|---|---|---|---|
| CN | 102459196 | A | 5/2012 |
| CN | 103328470 | A | 9/2013 |
| CN | 104356109 | A | 2/2015 |
| KR | 20090050044 | A | 5/2009 |
| WO | 0196311 | A2 | 12/2001 |
| WO | 02098854 | A2 | 12/2002 |
| WO | 2010140765 | A2 | 12/2010 |

*Primary Examiner* — Kahsay Habte

(57) ABSTRACT

Disclosed herein relates to organic synthesis, and more particularly to a method for preparing a key intermediate for the synthesis of statins. The key intermediate is 2-[(4R,6S)-6-[(benzo[d]thiazol-2-ylthio)methyl]-2,2-disubstituted-1,3-dioxan-4-yl] acetate of formula (I):

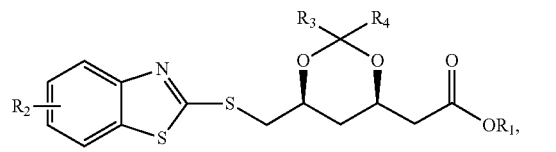

(I)

where $R_1$ is a $C_1$-$C_8$ alkyl group, a $C_3$-$C_8$ cycloalkyl group, a monosubstituted or polysubstituted aryl group, or monosubstituted or polysubstituted aralkyl group; $R_2$ is hydrogen, or monosubstituted or polysubstituted $C_1$-$C_3$ alkyl group, or halogen; and $R_3$ and $R_4$ are each independently a $C_1$-$C_5$ alkyl group, a $C_3$-$C_7$ cycloalkyl group, a $C_3$-$C_7$ cycloalkenyl group, a $C_1$-$C_3$ alkoxy group, a $C_6$-$C_{10}$ aryl group, or $C_7$-$C_{12}$ aralkyl group. In the method, a halomethyl compound and a thiol reagent are subjected to nucleophilic substitution in an organic solvent to synthesize a thioether, which then undergoes ketal exchange reaction with a carbonyl compound (V) in the presence of an organic acid to obtain a target product.

16 Claims, No Drawings

METHOD FOR PREPARING A KEY INTERMEDIATE FOR THE SYNTHESIS OF STATINS

CROSS-REFERENCE TO RELATED APPLICATIONS

This application claims the benefit of priority from Chinese Patent Application No. 202011064252.2, filed on Sep. 30, 2020. The content of the aforementioned application, including any intervening amendments thereto, is incorporated herein by reference in its entirety.

TECHNICAL FIELD

This disclosure relates to organic synthesis, and more particularly to a method for preparing a key intermediate for the synthesis of statins.

BACKGROUND

2-[(4R,6S)-6-[(benzo[d]thiazol-2-ylthio)methyl]-2,2-disubstituted-1,3-dioxan-4-yl] acetate (I) is a key intermediate for the synthesis of statins.

World patent Nos. 2001096311 and 2002098854 both disclosed a method of synthesizing 2-[(4R,6S)-6-[(benzo[d]thiazol-2-ylthio)-methyl]-2,2-dimethyl-1,3-dioxan-4-yl] acetate (I) by subjecting a sulfonyl hydroxymethyl ketal ester (Kaneka alcohol sulfonate) and 2-mercaptobenzothiazole to SN2 thionucleophilic substitution under alkaline conditions.

In addition, World patent No. 2010140765 and US patent No. 20120136151, Korean patent No. 1020090050044 and Chinese patent publication No. 102459196A all employed the SN2 thionucleophilic substitution of a halomethyl ketal ester and 2-mercaptobenzothiazole or a salt thereof to synthesize 2-((4R,6S)-6-[(benzo[d]thiazol-2-ylthio)-methyl]-2,2-dimethyl-1,3-dioxan-4-yl)acetate (I).

However, the above-mentioned methods all use a C6-hydroxymethyl ketal ester (Kaneka alcohol) as a chiral intermediate, whose preparation has complicated operation, high cost and large energy consumption due to the existence of multiple low-temperature reactions (−78° C.). Therefore, these strategies are not suitable for industrial applications.

SUMMARY

An object of this disclosure is to provide a simple and economical method for preparing a key intermediate for the synthesis of statins with high yield and purity to overcome the defects in the prior art.

Technical solutions of this disclosure are illustrated as follows.

This disclosure provides a method for preparing 2-[(4R,6S)-6-[(benzo[d]thiazol-2-ylthio)methyl]-2,2-disubstituted-1,3-dioxan-4-yl] acetate of formula (I):

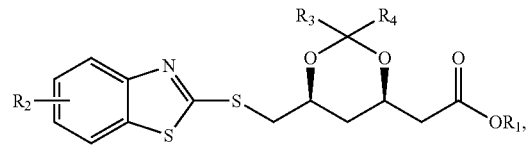

(I)

wherein $R_1$ is a $C_1$-$C_8$ alkyl group, $C_3$-$C_8$ cycloalkyl group, monosubstituted and polysubstituted aryl and monosubstituted and polysubstituted aralkyl; $R_2$ is hydrogen, a monosubstituted or polysubstituted $C_1$-$C_3$ alkyl group, or halogen; and $R_3$ and $R_4$ are each independently a $C_1$-$C_5$ alkyl group, a $C_3$-$C_7$ cycloalkyl group, a $C_3$-$C_7$ cycloalkenyl group, a $C_1$-$C_3$ alkoxy group, a $C_6$-$C_{10}$ aryl group, or a $C_7$-$C_{12}$ aralkyl group;

wherein the method comprising:

(1) subjecting a halomethyl compound and a thiol reagent to nucleophilic substitution in an organic solvent to synthesize a thioether; and (2) subjecting the thioether and a carbonyl compound to ketal exchange reaction in the presence of an organic acid to synthesize the 2-[(4R,6S)-6-[(benzo[d]thiazol-2-ylthio)methyl]-2,2-disubstituted-1,3-dioxan-4-yl] acetate (I).

In some embodiments, in step (1), the halomethyl compound is 2-[(4R,6S)-6-halomethyl-2-oxo-1,3-dioxan-4-yl] acetate of formula (II):

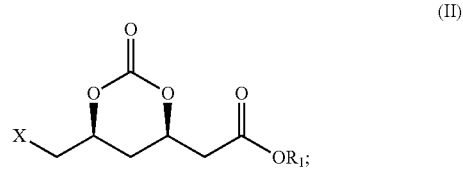

(II)

wherein X is halogen; and $R_1$ is a $C_1$-$C_8$ alkyl group, a $C_3$-$C_8$ cycloalkyl, a monosubstituted or polysubstituted aryl group, or a monosubstituted or polysubstituted aralkyl group;

the thiol reagent is a 2-mercaptobenzothiazole compound of formula (III):

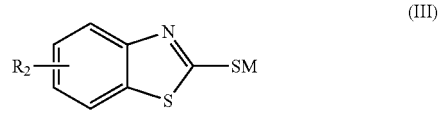

(III)

wherein $R_2$ is hydrogen, a monosubstituted or polysubstituted $C_1$-$C_3$ alkyl group, or halogen; and M is hydrogen, alkali metal cation, ammonium ion or phosphonium ion; and the thioether synthesized from the nucleophilic substitution is 2-[(4R,6S)-6-[(benzo[d]thiazol-2-ylthio)methyl]-2-oxo-1,3-dioxan-4-yl] acetate of formula (IV):

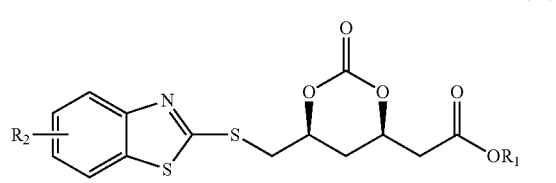

(IV)

wherein $R_1$ is a $C_1$-$C_8$ alkyl group, a $C_3$-$C_8$ cycloalkyl group, a $C_6$-$C_{10}$ aryl group, or a $C_7$-$C_{12}$ aralkyl group; and $R_2$ is hydrogen, a monosubstituted or polysubstituted $C_1$-$C_3$ alkyl group, or halogen.

In some embodiments, the thiol reagent is 2-mercaptobenzothiazole;

the step (1) specifically comprises:

subjecting 2-[(4R,6S)-6-halomethyl-2-oxo-1,3-dioxan-4-yl] acetate (II) and 2-mercaptobenzothiazole to nucleophilic substitution in the organic solvent in the presence of a base to synthesize the thioether;

wherein the base is an inorganic base or an organic base; the inorganic base is alkali metal carbonate, alkali metal bicarbonate, alkali metal hydroxide or a combination thereof; and the organic base is sodium methoxide, sodium ethoxide, sodium tert-butoxide, potassium tert-butoxide, triethylamine, pyridine or a combination thereof.

In some embodiments, when the M in the formula (III) is hydrogen, the base in step (1) is an inorganic base; the inorganic base is lithium carbonate, sodium carbonate, potassium carbonate, cesium carbonate, lithium bicarbonate, sodium bicarbonate, potassium bicarbonate, lithium hydroxide, sodium hydroxide or potassium hydroxide; or when the thiol reagent is a 2-mercaptobenzothiazole salt, the nucleophilic substitution in step (1) is performed in the absence of the base.

In some embodiments, in step (1), the organic solvent is a polar aprotic solvent or an ionic liquid.

In some embodiments, the organic solvent is N,N-dimethylformamide, dimethyl sulfoxide, N-methylpyrrolidone, sulfolane, 1,3-dimethyl-2-imidazolidinone, hexamethylphosphoric triamide, acetonitrile, a ketone solvent, N-alkylpyridinium salt, 1,3-dialkyl imidazolium salt or a combination thereof.

In some embodiments, the organic solvent is a ketone solvent. The suitable ketone solvents may include symmetric alkyl ketone, symmetric cycloalkyl ketone, asymmetric alkyl ketone, asymmetric cycloalkyl ketone, symmetric monosubstituted or polysubstituted aryl ketone, symmetric monosubstituted or polysubstituted aralkyl ketone, asymmetric monosubstituted or polysubstituted aryl ketone, asymmetric monosubstituted or polysubstituted aralkyl ketone or a combination thereof.

In some embodiments, the ketone solvent is acetone, butanone, phenylacetone, cyclohexanone, methyl propyl ketone, 2-methyl cyclohexanone, benzophenone, 4-methyl benzophenone, 4-methyl-1-phenyl-2-pentanone or cyclopropyl methyl ketone.

In some embodiments, the ketone solvent is acetone.

In some embodiments, in step (1), a concentration of the halomethyl compound is 0.1-5 mol/L.

In some embodiments, in step (1), a molar ratio of the halomethyl compound to the thiol reagent is 1:0.5-5.

In some embodiments, in step (1), the molar ratio of the halomethyl compound to the thiol reagent is 1:1-3.

In some embodiments, in step (1), the nucleophilic substitution is performed at 20-180° C. for 1-18 h.

In some embodiments, in step (1), the nucleophilic substitution is performed at 30-90° C. for 4-10 h.

In some embodiments, in step (2), the carbonyl compound is a ketone compound of formula (V):

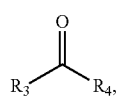

(V)

wherein $R_3$ and $R_4$ are each independently a $C_1$-$C_5$ alkyl group, a $C_3$-$C_7$ cycloalkyl group, a $C_3$-$C_7$ cycloalkenyl group, a $C_1$-$C_3$ alkoxy group, a $C_6$-$C_{10}$ aryl group, or a $C_7$-$C_{12}$ aralkyl group.

In some embodiments, in step (2), the organic acid is p-toluenesulfonic acid, methanesulfonic acid, benzenesulfonic acid or camphor sulfonic acid.

In some embodiments, in step (2), the organic acid is p-toluenesulfonic acid or benzenesulfonic acid.

In some embodiments, in step (2), a concentration of the thioether is 0.1-5 mol/L.

In some embodiments, in step (2), a molar ratio of the thioether to the organic acid is 1:0.01-5.

In some embodiments, in step (2), the molar ratio of the thioether to the organic acid is 1:0.1-1.

In some embodiments, in step (2), the ketal exchange reaction is performed at 10-80° C. for 1-48 h.

In some embodiments, in step (2), the ketal exchange reaction is performed at 15-50° C. for 3-10 h.

The above-mentioned preparation process, in which a halomethyl compound and a thiol reagent are subjected to nucleophilic substitution in an organic solvent to synthesize a thioether, and then the thioether and a carbonyl compound are subjected to a ketal exchange reaction in the presence of an organic acid to produce 2-[(4R,6S)-6-[(benzo[d]thiazol-2-ylthio)-methyl]-2,2-disubstituted-1,3-dioxan-4-yl] acetate (I), has mild reaction conditions, low cost, simple operation (e.g., no need for anhydrous and oxygen-free conditions, no need for extreme cold or cryogenic conditions, simple workup procedure, etc.), high total yield (>90%) and good product quality, and thus has a brilliant application prospect. Notably, the present invention allows "one-pot" preparation of the target compound 2-[(4R,6S)-6-[(benzo[d]thiazol-2-ylthio)-methyl]-2,2-disubstituted-1,3-dioxan-4-yl] acetate (I).

The synthetic route of the above preparation process is shown as follows.

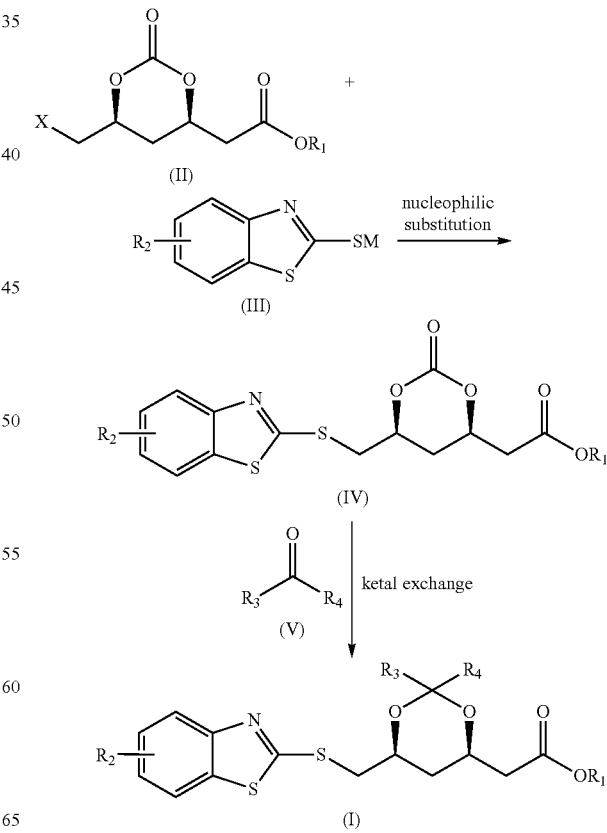

DETAILED DESCRIPTION OF EMBODIMENTS

In order to make the technical solutions, structural features, objectives and beneficial effects of this disclosure clear, this disclosure will be illustrated in detail below with reference to the embodiments. It should be noted that the following embodiments are merely illustrative of the disclosure, and are not intended to limit the disclosure.

This disclosure provides a method for preparing 2-[(4R,6S)-6-[(benzo[d]thiazol-2-ylthio)methyl]-2,2-disubstituted-1,3-dioxan-4-yl] acetate of formula (I):

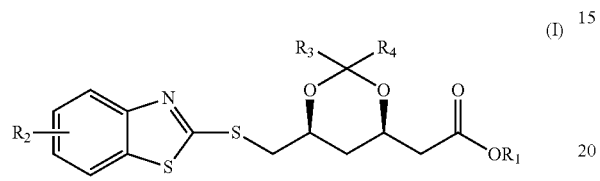

(I)

wherein $R_1$ is a $C_1$-$C_8$ alkyl group, a $C_3$-$C_8$ cycloalkyl group, a monosubstituted or polysubstituted aryl group or a monosubstituted or polysubstituted aralkyl group; $R_2$ is hydrogen, a monosubstituted or polysubstituted $C_1$-$C_3$ alkyl, or halogen; and $R_3$ and $R_4$ are each independently a $C_1$-$C_5$ alkyl group, a $C_3$-$C_7$ cycloalkyl group, a $C_3$-$C_7$ cycloalkenyl group, a $C_1$-$C_3$ alkoxy group, a $C_6$-$C_{10}$ aryl group, or a $C_7$-$C_{12}$ aralkyl group;

the method includes:

(1) subjecting a halomethyl compound and a thiol reagent to nucleophilic substitution in an organic solvent to synthesize a thioether; and (2) subjecting the thioether and a carbonyl compound to ketal exchange reaction in the presence of an organic acid to synthesize the 2-[(4R,6S)-6-[(benzo[d]thiazol-2-ylthio)methyl]-2,2-disubstituted-1,3-dioxan-4-yl] acetate (I), where a yield of the 2-[(4R,6S)-6-[(benzo[d]thiazol-2-ylthio)methyl]-2,2-disubstituted-1,3-dioxan-4-yl] acetate (I) is more than 90%.

The synthetic route of the above preparation process is shown as follows:

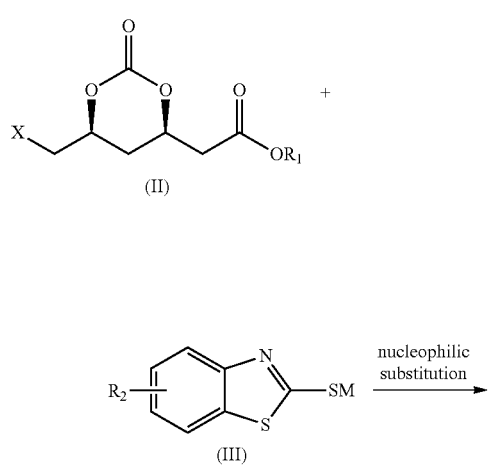

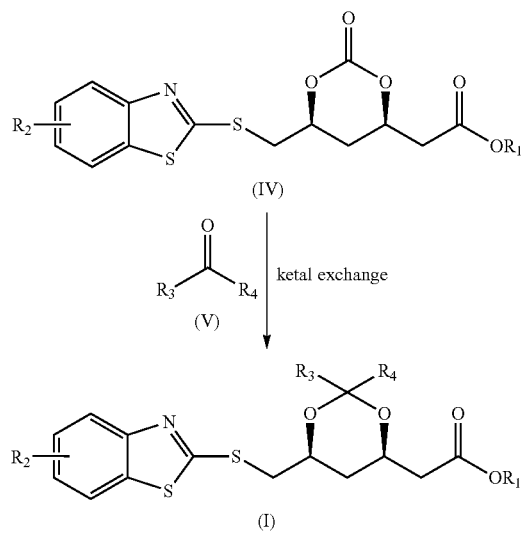

where X is halogen, such as chlorine (Cl), bromine (Br) and iodine (I); $R_1$ is a $C_1$-$C_8$ alkyl group, a $C_3$-$C_8$ cycloalkyl group, a $C_6$-$C_{10}$ aryl group or a $C_7$-$C_{12}$ aralkyl group; $R_2$ is hydrogen, a monosubstituted or polysubstituted $C_1$-$C_3$ alkyl group, or halogen; and $R_3$ and $R_4$ are each independently a $C_1$-$C_{12}$ alkyl group, a $C_3$-$C_7$ cycloalkyl group, a $C_1$-$C_3$ alkoxy group, a $C_3$-$C_7$ cycloalkenyl group, a $C_6$-$C_{10}$ aryl group, or a $C_7$-$C_{12}$ aralkyl group.

In some embodiments, in step (1), the halomethyl compound is 2-[(4R,6S)-6-halomethyl-2-oxo-1,3-dioxan-4-yl] acetate of formula (II):

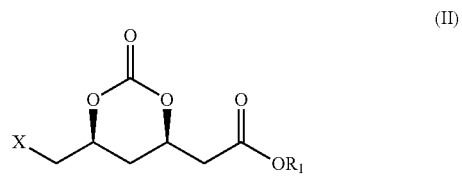

(II)

in the formula, X is halogen, such as Cl, Br and I, and $R_1$ is a $C_1$-$C_8$ alkyl group, a $C_3$-$C_8$ cycloalkyl group, a monosubstituted or polysubstituted aryl group, a monosubstituted or polysubstituted aralkyl group;

the thiol reagent is a 2-mercaptobenzothiazole compound of formula (III):

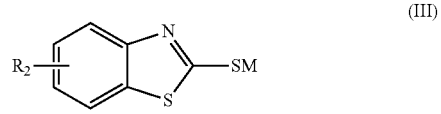

(III)

in the formula, $R_2$ is a monosubstituted or polysubstituted $C_1$-$C_3$ alkyl group, or halogen; and M is hydrogen, alkali metal cation, ammonium ion or phosphonium ion; and the thioether synthesized from the nucleophilic substitution is 2-[(4R,6S)-6-[(benzo[d]thiazol-2-ylthio)methyl]-2-oxo-1,3 oxan-4-yl] acetate of formula (IV):

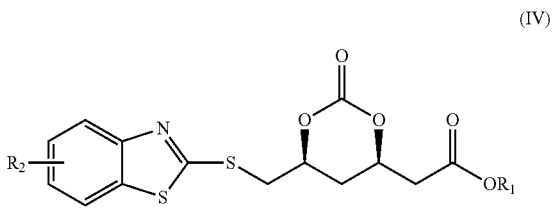

(IV)

in the formula, $R_1$ is a $C_1$-$C_8$ alkyl group, a $C_3$-$C_8$ cycloalkyl group, a $C_6$-$C_{10}$ aryl group, or a $C_7$-$C_{12}$ aralkyl group; and $R_2$ is hydrogen, a monosubstituted or polysubstituted $C_1$-$C_3$ alkyl group, or halogen.

In some embodiments, when the thiol reagent is 2-mercaptobenzothiazole, the nucleophilic substitution is performed in the presence of a base. The base is an inorganic base or an organic base. The inorganic base is alkali metal carbonate, alkali metal bicarbonate, alkali metal hydroxide or a combination thereof, such as lithium carbonate, sodium carbonate, potassium carbonate, lithium bicarbonate, sodium bicarbonate, potassium bicarbonate, lithium hydroxide, sodium hydroxide or potassium hydroxide. The organic base is sodium methoxide, sodium ethoxide, sodium tert-butoxide, potassium tert-butoxide, triethylamine, pyridine or a combination thereof.

In some embodiments, when the M in the formula (III) is hydrogen, the base used in the nucleophilic substitution in step (1) is an inorganic base; exemplary inorganic bases include lithium carbonate, sodium carbonate, potassium carbonate, cesium carbonate, lithium bicarbonate, sodium bicarbonate, potassium bicarbonate, lithium hydroxide, sodium hydroxide or potassium hydroxide.

In some embodiments, when the thiol reagent is a 2-mercaptobenzothiazole salt, the nucleophilic substitution in step (1) can be performed in a base-free condition.

In some embodiments, in step (1), the organic solvent is a polar aprotic solvent or an ionic liquid. The organic solvent is N,N-dimethylformamide, dimethyl sulfoxide, N-methylpyrrolidone, sulfolane, 1,3-dimethyl-2-imidazolidinone, hexamethylphosphoric triamide, acetonitrile, a ketone solvent, N-alkylpyridinium salt, 1,3-dialkyl imidazolium salt or a combination thereof.

In some embodiments, in the nucleophilic substitution, a concentration of the halomethyl compound is 0.1-5 mol/L.

In some embodiments, in the nucleophilic substitution, a molar ratio of the halomethyl compound to the thiol reagent is 1:0.5-5.

In some embodiments, the nucleophilic substitution is performed at 20-180° C. for 1-18 h.

In some embodiments, the nucleophilic substitution is performed under the following conditions.

1) When the thiol reagent is 2-mercaptobenzothiazole, a better reaction result will be obtained in the presence of an inorganic base, where the inorganic base is an alkali metal carbonate, such as lithium carbonate, sodium carbonate, potassium carbonate or cesium carbonate, preferably potassium carbonate or sodium carbonate, which is cheap and readily available.

2) When the organic solvent is a ketone solvent, after completion of the nucleophilic substitution reaction in step (1), an organic acid can be directly added into the reaction mixture to prepare the target compound (I) without the need to isolate the intermediate compound (IV), thus allowing for a one-pot process for the preparation of the compound (I). The desired ketone solvents include symmetric alkyl ketone, symmetric cycloalkyl ketone, asymmetric alkyl ketone, asymmetric cycloalkyl ketone, symmetric monosubstituted or polysubstituted aryl ketone, symmetric monosubstituted or polysubstituted aralkyl ketone, asymmetric monosubstituted or polysubstituted aryl ketone, asymmetric monosubstituted or polysubstituted aralkyl ketone, such as, acetone, butanone, phenylacetone, cyclohexanone, methyl propyl ketone, 2-methyl cyclohexanone, benzophenone, 4-methyl benzophenone, 4-methyl-1-phenyl-2-pentanone and cyclopropyl methyl ketone, preferably acetone, which is cheap, safe, non-toxic and recyclable.

3) The molar ratio of the halomethyl compound to the thiol reagent is 1:1-3, and the nucleophilic substitution is performed at 30-90° C. for 4-10 h.

In some embodiments, in the ketal exchange reaction, the carbonyl compound is a ketone compound of formula (V):

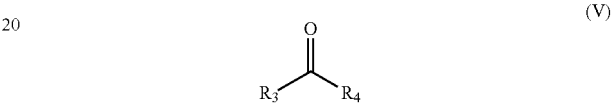

(V)

in the formula, $R_3$ and $R_4$ are each independently a $C_1$-$C_5$ alkyl group, a $C_3$-$C_7$ cycloalkyl group, a $C_3$-$C_7$ cycloalkenyl group, a $C_1$-$C_3$ alkoxy group, a $C_6$-$C_{10}$ aryl group, or a $C_7$-$C_{12}$ aralkyl group.

In some embodiments, the organic acid in the ketal exchange reaction is p-toluenesulfonic acid, methanesulfonic acid, benzenesulfonic acid or camphor sulfonic acid.

In some embodiments, in the ketal exchange reaction, a concentration of the thioether is 0.1-5 mol/L.

In some embodiments, in the ketal exchange reaction, a molar ratio of the thioether to the organic acid is 1:0.1-5.

In some embodiments, the ketal exchange reaction is performed at 10-80° C. for 1-48 h.

In some embodiments, the ketal exchange reaction is performed under the following conditions.

1) The ketone compound (V) is acetone, which has good reactivity and can lower the reaction temperature. If the solvent used in the nucleophilic substitution is acetone, the nucleophilic substitution and the ketal exchange reaction can be carried out using a one-pot method, simplifying the operation process.

2) The organic acid is p-toluenesulfonic acid or benzenesulfonic acid, which gives an optimal performance.

3) The molar ratio of the thioether to the organic acid is 1:0. 1-1. The ketal exchange reaction is performed at 15-50° C., preferably at 15-35° C., and more preferably 20-30° C., for 3-10 h.

In the above-mentioned technical solutions, 2-[(4R,6S)-6-halomethyl-2-oxo-1,3-dioxan-4-yl] acetate (II) is first reacted with a 2-mercaptobenzothiazole (III) to form 2-[(4R,6S)-6-[(benzo[d]thiazol-2-ylthio)methyl]-2-oxo-1,3-dioxan-4-yl) acetate (IV), which is then subjected to a ketal exchange reaction with a carbonyl compound (V) to produce 2-[(4R,6S)-6-[(benzo[d]thiazol-2-ylthio)-methyl]-2,2-disubstituted-1,3-dioxan-4-yl] acetate (I). This method has mild reaction conditions, low cost, simple operation (e.g., no need for anhydrous and oxygen-free conditions, no need for extreme cold or cryogenic conditions, simple workup procedure, etc.), high total yield (>90%) and excellent purity, and thus it is promising in the industrial application.

Reference will be made to the following embodiments to describe the disclosure in detail. Unless otherwise specified, the materials and reagents used in the embodiments are all commercially available.

Example 1 Preparation of tert-butyl 2-[(4R,6S)-6-[(benzo[d]thiazol-2-ylthio)methyl]-2-oxo-1,3-dioxan-4-yl)] acetate (IV)

Tert-butyl 2-[(4R,6S)-6-bromomethyl-2-oxo-1,3-dioxan-4-yl] acetate (30.9 g, 0.1 mol), sodium 2-mercaptobenzothiazole (20.8 g, 0.11 mol) and N, N-dimethylformamide (150 mL) were added into a reaction flask. The reaction mixture was heated to 70° C. and reacted under stirring for 6 h. Then the reaction mixture was cooled, and subjected to vacuum concentration to recover the N, N-dimethylformamide. The residue was added with ethyl acetate (300 mL) and water (150 mL), and stirred for 10 min. An organic phase was separated, and washed sequentially with saturated sodium bicarbonate solution (100 mL) and saturated sodium chloride solution (100 mL), and then vacuum concentrated to obtain the compound (IV) (38.8 g, 98% yield).

The compound IV was characterized as follows:
mp 82.2-84.5° C.;
$[\alpha]25D=-23.48$ (c=1.0, CHCl$_3$);
mass spectrum m/z 396.09 (MH+);
$^1$H NMR (400 MHz, CDCl$_3$): δ 7.87 (d, J=7.9 Hz, 1H), 7.78 (d, J=7.7 Hz, 1H), 7.47-7.43 (m, 1H), 7.36-7.32 (m, 1H), 4.98-4.91 (m, 1H), 4.89-4.82 (m, 1H), 3.84-3.79 (m, 1H), 3.66-3.61 (m, 1H), 2.79-2.73 (m, 1H), 2.59-2.49 (m, 2H), 1.92-1.83 (m, 1H), 1.45 (s, 9H); and
$^{13}$C NMR (101 MHz, CDCl$_3$): δ 168.2, 164.9, 152.7, 148.1, 135.5, 126.2, 124.7, 121.6, 121.2, 82.0, 75.0, 40.9, 36.3, 31.4, 28.0.

Example 2 Preparation of tert-butyl 2-[(4R,6S)-6-[(benzo[d]thiazol-2-ylthio)methyl]-2-oxo-1,3-dioxan-4-yl)] acetate (IV)

Tert-butyl 2-[(4R,6S)-6-chloromethyl-2-oxo-1,3-dioxan-4-yl] acetate (26.5 g, 0.1 mol), sodium 2-mercaptobenzothiazole (20.8 g, 0.11 mol) and N, N-dimethylformamide (150 mL) were added into a reaction flask. The reaction mixture was heated to 70° C. and reacted under stirring for 6 h. Then the reaction mixture was cooled, and subjected to vacuum concentration to recover the N, N-dimethylformamide. The residue was added with ethyl acetate (300 mL) and water (150 mL), and stirred for 10 min. An organic phase was separated, and washed sequentially with saturated sodium bicarbonate solution (100 mL) and saturated sodium chloride solution (100 mL), and then vacuum concentrated to obtain the compound (IV) (37.97 g, 96% yield).

Example 3 Preparation of methyl 2-[(4R,6S)-6-[(benzo[d]thiazol-2-ylthio)methyl]-2-oxo-1,3-dioxan-4-yl] acetate (IV)

Methyl 2-[(4R,6S)-6-bromomethyl-2-oxo-1,3-dioxan-4-yl] acetate (22.3 g, 0.1 mol), sodium 2-mercaptobenzothiazole (20.8 g, 0.11 mol) and N, N-dimethylformamide (150 mL) were added into a reaction flask. The reaction mixture was heated to 70° C. and reacted under stirring for 6 h. Then the reaction mixture was cooled, and subjected to vacuum concentration to recover the N, N-dimethylformamide. The residue was added with ethyl acetate (300 mL) and water (150 mL), and stirred for 10 min. An organic phase was separated, and washed sequentially with saturated sodium bicarbonate solution (100 mL) and saturated sodium chloride solution (100 mL), and then vacuum concentrated to obtain the compound (IV) (34.28 g, 97% yield).

Example 4 Preparation of ethyl 2-[(4R,6S)-6-[(benzo[d]thiazol-2-ylthio)methyl]-2-oxo-1,3-dioxan-4-yl] acetate (IV)

Ethyl 2-[(4R,6S)-6-bromomethyl-2-oxo-1,3-dioxan-4-yl] acetate (23.7 g, 0.1 mol), sodium 2-mercaptobenzothiazole (20.8 g, 0.11 mol) and N, N-dimethylformamide (150 mL) were added into a reaction flask. The reaction mixture was heated to 70° C. and reacted under stirring for 6 h. Then the reaction mixture was cooled, and subjected to vacuum concentration to recover the N, N-dimethylformamide. The residue was added with ethyl acetate (300 mL) and water (150 mL), and stirred for 10 min. An organic phase was separated, and washed sequentially with saturated sodium bicarbonate solution (100 mL) and saturated sodium chloride solution (100 mL), and then vacuum concentrated to obtain the compound (IV) (35.64 g, 97% yield).

Example 5 Preparation of n-hexyl 2-[(4R,6S)-6-[(benzo[d]thiazol-2-ylthio)methyl]-2-oxo-1,3-dioxan-4-yl] acetate (IV)

n-hexyl 2-[(4R,6S)-6-bromomethyl-2-oxo-1,3-dioxan-4-yl] acetate (29.3 g, 0.1 mol), sodium 2-mercaptobenzothiazole (20.8 g, 0.11 mol) and N, N-dimethylformamide (150 mL) were added into a reaction flask. The reaction mixture was heated to 70° C. and reacted under stirring for 6 h. Then the reaction mixture was cooled, and subjected to vacuum concentration to recover the N, N-dimethylformamide. The residue was added with ethyl acetate (300 mL) and water (150 mL), and stirred for 10 min. An organic phase was separated, and washed sequentially with saturated sodium bicarbonate solution (100 mL) and saturated sodium chloride solution (100 mL), and then vacuum concentrated to obtain the compound (IV) (41.72 g, 98.5% yield).

Example 6 Preparation of cyclohexyl 2-[(4R,6S)-6-[(benzo[d]thiazol-2-ylthio)methyl]-2-oxo-1,3-dioxan-4-yl] acetate (IV)

Cyclohexyl 2-[(4R,6S)-6-bromomethyl-2-oxo-1,3-dioxan-4-yl] acetate (29.1 g, 0.1 mol), sodium 2-mercaptobenzothiazole (20.8 g, 0.11 mol) and N, N-dimethylformamide (150 mL) were added into a reaction flask. The reaction mixture was heated to 70° C. and reacted under stirring for 6 h. Then the reaction mixture was cooled, and subjected to vacuum concentration to recover the N, N-dimethylformamide. The residue was added with ethyl acetate (300 mL) and water (150 mL), and stirred for 10 min. An organic phase was separated, and washed sequentially with saturated sodium bicarbonate solution (100 mL) and saturated sodium chloride solution (100 mL), and then vacuum concentrated to obtain the compound (IV) (41.39 g, 98.2% yield).

Example 7 Preparation of benzyl 2-[(4R,6S)-6-[(benzo[d]thiazol-2-ylthio)methyl]-2-oxo-1,3-dioxan-4-yl] acetate (IV)

Benzyl 2-[(4R,6S)-6-bromomethyl-2-oxo-1,3-dioxan-4-yl] acetate (29.9 g, 0.1 mol), sodium 2-mercaptobenzothiazole (20.8 g, 0.11 mol) and N, N-dimethylformamide (150 mL) were added into a reaction flask. The reaction mixture was heated to 70° C. and reacted under stirring for 6 h. Then the reaction mixture was cooled, and subjected to vacuum concentration to recover the N, N-dimethylformamide. The residue was added with ethyl acetate (300 mL) and water (150 mL), and stirred for 10 min. An organic phase was separated, and washed sequentially with saturated sodium bicarbonate solution (100 mL) and saturated sodium chloride solution (100 mL), and then vacuum concentrated to obtain the compound (IV) (42.22 g, 98.3% yield).

Example 8 Preparation of tert-butyl 2-[(4R,6S)-6-[(benzo[d]thiazol-2-ylthio)methyl]-2-oxo-1,3-dioxan-4-yl] acetate (IV)

Tert-butyl 2-[(4R,6S)-6-bromomethyl-2-oxo-1,3-dioxan-4-yl] acetate (30.9 g, 0.1 mol), sodium 2-mercaptobenzothiazole (20.8 g, 0.11 mol) and dimethyl sulfoxide (150 mL) were added into a reaction flask. The reaction mixture was heated to 60° C. and reacted under stirring for 7 h. Then the reaction mixture was cooled, and subjected to vacuum concentration to recover the dimethyl sulfoxide. The residue was added with ethyl acetate (300 mL) and water (150 mL), and stirred for 10 min. An organic phase was separated, and washed sequentially with saturated sodium bicarbonate solution (100 mL) and saturated sodium chloride solution (100 mL), and then vacuum concentrated to obtain the compound (IV) (38.6 g, 97.6% yield).

Example 9 Preparation of tert-butyl 2-[(4R,6S)-6-[(benzo[d]thiazol-2-ylthio)methyl]-2-oxo-1,3-dioxan-4-yl] acetate (IV)

Tert-butyl 2-[(4R,6S)-6-bromomethyl-2-oxo-1,3-dioxan-4-yl] acetate (30.9 g, 0.1 mol), sodium 2-mercaptobenzothiazole (20.8 g, 0.11 mol) and N-methylpyrrolidone (150 mL) were added into a reaction flask. The reaction mixture was heated to 80° C. and reacted under stirring for 5 h. Then the reaction mixture was cooled, and subjected to vacuum concentration to recover the N-methylpyrrolidone. The residue was added with ethyl acetate (300 mL) and water (150 mL), and stirred for 10 min. An organic phase was separated, and washed sequentially with saturated sodium bicarbonate solution (100 mL) and saturated sodium chloride solution (100 mL), and then vacuum concentrated to obtain the compound (IV) (38.2 g, 96.6% yield).

Example 10 Preparation of Tert-butyl 2-[(4R,6S)-6-[(benzo[d]thiazol-2-ylthio)methyl]-2,2-disubstituted-1,3-dioxan-4-yl)] acetate (I)

The compound (IV) obtained in Example 1 (38.8 g, 0.098 mol), p-toluenesulfonic acid monohydrate (1.86 g, 0.0098 mol) and acetone (150 mL) were added into a reaction flask, and reacted under stirring at room temperature for 5 h. Then the reaction mixture was neutralized with saturated sodium bicarbonate solution and subjected to extraction with ethyl acetate (200 mL). An organic phase was separated and then vacuum concentrated to obtain the compound (I) (36.12 g, 90% yield).

The compound I was characterized as follows:
mp 70.8-71.9° C.;
[α]25D=+28.88 (c=1.0, CHCl$_3$);
mass spectrum m/z 410.14 (MH+);
$^1$H NMR (400 MHz, CDCl$_3$): δ 7.87 (d, J=8.1 Hz, 1H), 7.77 (d, J=7.8 Hz, 1H), 7.45-7.41 (m, 1H), 7.33-7.29 (m, 1H), 4.33-4.24 (m, 2H), 3.58-3.53 (m, 1H), 3.48-3.43 (m, 1H), 2.50-2.44 (m, 1H), 2.38-2.32 (m, 1H), 1.85 (m, 1H), 1.48 (s, 3H), 1.46 (s, 9H), 1.42 (s, 3H). $^{13}$C NMR (101 MHz, CDCl$_3$); and
δ 170.1, 166.8, 153.1, 135.3, 126.0, 124.3, 121.5, 121.0, 99.3, 80.7, 68.2, 66.1, 42.6, 38.5, 35.4, 29.9, 28.1, 19.8.

Example 11 Preparation of tert-butyl 2-[(4R,6S)-6-[(benzo[d]thiazol-2-ylthio)methyl]-2,2-disubstituted-1,3-dioxan-4-yl)] acetate (I)

The compound (IV) (38.8 g, 0.098 mol) obtained in Example 1, benzenesulfonic acid monohydrate (1.73 g, 0.0098 mol) and acetone (150 mL) were added to a reaction flask, and reacted under stirring at room temperature for 5 h. Then the reaction mixture was neutralized with saturated sodium bicarbonate solution and subjected to extraction with ethyl acetate (200 mL). An organic phase was separated and then vacuum concentrated to obtain the compound (I) (36.52 g, 91% yield).

Example 12 Preparation of tert-butyl 2-[(4R,6S)-6-[(benzo[d]thiazol-2-ylthio)methyl]-2,2-disubstituted-1,3-dioxan-4-yl)] acetate (I)

The compound (IV) (38.8 g, 0.098 mol) obtained in Example 1, camphorsulfonic acid (2.28 g, 0.0098 mol) and acetone (150 mL) were added to a reaction flask, and reacted under stirring at room temperature for 6 h. Then the reaction mixture was neutralized with saturated sodium bicarbonate solution and subjected to extraction with ethyl acetate (200 mL). An organic phase was separated and then vacuum concentrated to obtain the compound (I) (36.92 g, 92% yield).

Example 13 Preparation of tert-butyl 2-[(4R,6S)-6-[(benzo[d]thiazol-2-ylthio)methyl]-2-oxo-1,3-dioxan-4-yl] acetate (IV)

Tert-butyl 2-[(4R,6S)-6-bromomethyl-2-oxo-1,3-dioxan-4-yl] acetate (30.9 g, 0.1 mol), 2-mercaptobenzothiazole (18.4 g, 0.11 mol), potassium carbonate (15.2 g, 0.11 mol) and N, N-dimethylformamide (150 mL) were added into a reaction flask. The reaction mixture was heated to 70° C. and reacted under stirring for 6 h. Then the reaction mixture was cooled, and subjected to vacuum concentration to recover the N, N-dimethylformamide. The residue was added with ethyl acetate (300 mL) and water (150 mL), and stirred for 10 min. An organic phase was separated, and washed sequentially with saturated sodium bicarbonate solution (100 mL) and saturated sodium chloride solution (100 mL), and then vacuum concentrated to obtain the compound (IV) (37.97 g, 96% yield).

Example 14 Preparation of tert-butyl 2-[(4R,6S)-6-[(benzo[d]thiazol-2-ylthio)methyl]-2-oxo-1,3-dioxan-4-yl] acetate (IV)

The method provided in this example was the same as that in Example 13 except that the potassium carbonate was replaced with sodium carbonate of the same mole number. In this example, 37.97 g of the compound (IV) was obtained (96% yield).

Example 15 Preparation of tert-butyl 2-[(4R,6S)-6-[(benzo[d]thiazol-2-ylthio)methyl]-2-oxo-1,3-dioxan-4-yl] acetate (IV)

The method provided in this example was the same as that in Example 13 except that the potassium carbonate was

Example 16 Preparation of tert-butyl 2-[(4R,6S)-6-[(benzo[d]thiazol-2-ylthio)methyl]-2-oxo-1,3-dioxan-4-yl] acetate (IV)

The method provided in this example was the same as that in Example 13 except that the potassium carbonate was replaced with sodium bicarbonate of the same mole number. In this example, 37.65 g of the compound (IV) was obtained (95.2% yield).

Example 17 Preparation of tert-butyl 2-[(4R,6S)-6-[(benzo[d]thiazol-2-ylthio)methyl]-2-oxo-1,3-dioxan-4-yl] acetate (IV)

The method provided in this example was the same as that in Example 13 except that the potassium carbonate was replaced with sodium tert-butoxide of the same mole number. In this example, 36.78 g of the compound (IV) was obtained (93% yield).

Example 18 Preparation of tert-butyl 2-[(4R,6S)-6-[(benzo[d]thiazol-2-ylthio)methyl]-2-oxo-1,3-dioxan-4-yl] acetate (IV)

The method provided in this example was the same as that in Example 13 except that the potassium carbonate was replaced with sodium ethoxide of the same mole number. In this example, 36.94 g of the compound (IV) was obtained (93.4% yield).

Example 19 Preparation of tert-butyl 2-[(4R,6S)-6-[(benzo[d]thiazol-2-ylthio)methyl]-2,2-disubstituted-1,3-dioxan-4-yl)] acetate (I)

The compound (IV) (38.0 g, 0.096 mol) obtained in Example 13, p-toluenesulfonic acid monohydrate (3.65 g, 0.0192 mol) and acetone (150 mL) were added into a reaction flask, and reacted under stirring at room temperature for 5 h. The reaction mixture was neutralized with saturated sodium bicarbonate solution and subjected to extraction with ethyl acetate (200 mL). An organic phase was separated and then vacuum concentrated to obtain the compound (I) (36.6 g, 93% yield).

Example 20 Preparation of tert-butyl 2-[(4R,6S)-6-[(benzo[d]thiazol-2-ylthio)methyl]-2,2-disubstituted-1,3-dioxan-4-yl)] acetate (I)

The compound (IV) (38.0 g, 0.096 mol) obtained in Example 13, p-toluenesulfonic acid monohydrate (9.13 g, 0.048 mol) and acetone (150 mL) were added into a reaction flask, and reacted under stirring at room temperature for 5 h. The reaction mixture was neutralized with saturated sodium bicarbonate solution and subjected to extraction with ethyl acetate (200 mL). An organic phase was separated and then vacuum concentrated to obtain the compound (I) (37.35 g, 95% yield).

Example 21 Preparation of tert-butyl 2-[(4R,6S)-6-[(benzo[d]thiazol-2-ylthio)methyl]-2,2-disubstituted-1,3-dioxan-4-yl)] acetate (I)

The compound (IV) (38.0 g, 0.096 mol) obtained in Example 13, p-toluenesulfonic acid monohydrate (14.6 g, 0.0768 mol) and acetone (150 mL) were added into a reaction flask, and reacted under stirring at room temperature for 5 h. The reaction mixture was neutralized with saturated sodium bicarbonate solution and subjected to extraction with ethyl acetate (200 mL). An organic phase was separated and then vacuum concentrated to obtain the compound (I) (37.55 g, 95.5% yield).

Example 22 Preparation of tert-butyl 2-[(4R,6S)-6-[(benzo[d]thiazol-2-ylthio)methyl]-2,2-disubstituted-1,3-dioxan-4-yl)] acetate (I)

Tert-butyl 2-[(4R,6S)-6-bromomethyl-2-oxo-1,3-dioxan-4-yl)] acetate (30.9 g, 0.1 mol), sodium 2-mercaptobenzothiazole (20.8 g, 0.11 mol) and acetone (150 mL) were added to a reaction flask. The reaction mixture was heated to 60° C. and reacted under stirring for 6 h. The reaction mixture was cooled to room temperature, added with p-toluenesulfonic acid monohydrate (3.65 g, 0.0192 mol) and reacted under stirring at room temperature for 5 h. Then the reaction mixture was neutralized with saturated sodium bicarbonate solution and subjected to extraction with ethyl acetate (200 mL). An organic phase was separated and then vacuum concentrated to obtain the compound (I) (38.9 g, 95% yield).

Example 23 Preparation of tert-butyl 2-[(4R,6S)-6-[(benzo[d]thiazol-2-ylthio)methyl]-2,2-disubstituted-1,3-dioxan-4-yl)] acetate (I)

Tert-butyl 2-[(4R,6S)-6-bromomethyl-2-oxo-1,3-dioxan-4-yl)] acetate (30.9 g, 0.1 mol), sodium 2-mercaptobenzothiazole (37.82 g, 0.2 mol) and acetone (150 mL) were added into a reaction flask. The reaction mixture was heated to 60° C. and reacted under stirring for 6 h. The reaction mixture was cooled to room temperature, added with p-toluenesulfonic acid monohydrate (3.65 g, 0.0192 mol) and reacted under stirring at room temperature for 5 h. Then the reaction mixture was neutralized with saturated sodium bicarbonate solution and subjected to extraction with ethyl acetate (200 mL). An organic phase was separated and then vacuum concentrated to obtain the compound (I) (38.9 g, 95.5% yield).

Example 24 Preparation of tert-butyl 2-[(4R,6S)-6-[(benzo[d]thiazol-2-ylthio)methyl]-2,2-disubstituted-1,3-dioxan-4-yl)] acetate (I)

Tert-butyl 2-[(4R,6S)-6-bromomethyl-2-oxo-1,3-dioxan-4-yl)] acetate (30.9 g, 0.1 mol), sodium 2-mercaptobenzothiazole (56.73 g, 0.3 mol) and acetone (150 mL) were added into a reaction flask. The reaction mixture was heated to 60° C. and reacted under stirring for 6 h. The reaction mixture was cooled to room temperature, added with p-toluenesulfonic acid monohydrate (3.65 g, 0.0192 mol) and reacted under stirring at room temperature for 5 h. Then the reaction mixture was neutralized with saturated sodium bicarbonate solution and subjected to extraction with ethyl acetate (200 mL). An organic phase was separated and then vacuum concentrated to obtain the compound (I) (39.24 g, 95.8% yield).

Example 25 Preparation of tert-butyl 2-[(4R,6S)-6-[(benzo[d]thiazol-2-ylthio)methyl]-2,2-disubstituted-1,3-dioxan-4-yl)] acetate (I)

Tert-butyl 2-[(4R,6S)-6-bromomethyl-2-oxo-1,3-dioxan-4-yl)] acetate (30.9 g, 0.1 mol), sodium 2-mercaptobenzo-

[continued: replaced with cesium carbonate of the same mole number. In this example, 37.85 g of the compound (IV) was obtained (95.7% yield).]

thiazole (9.45 g, 0.05 mol) and acetone (150 mL) were added into a reaction flask. The reaction mixture was heated to 60° C. and reacted under stirring for 6 h. The reaction mixture was cooled to room temperature, added with p-toluenesulfonic acid monohydrate (3.65 g, 0.0192 mol) and reacted under stirring at room temperature for 5 h. Then the reaction mixture was neutralized with saturated sodium bicarbonate solution and subjected to extraction with ethyl acetate (200 mL). An organic phase was separated and then vacuum concentrated to obtain then compound (I) (37.11 g, 90.6% yield).

Example 26 Preparation of tert-butyl 2-[(4R,6S)-6-[(benzo[d]thiazol-2-ylthio)methyl]-2,2-disubstituted-1,3-dioxan-4-yl)] acetate (I)

Tert-butyl 2-[(4R,6S)-6-bromomethyl-2-oxo-1,3-dioxan-4-yl)] acetate (30.9 g, 0.1 mol), 2-mercaptobenzothiazole (18.4 g, 0.11 mol), potassium carbonate (15.2 g, 0.11 mol) and acetone (150 mL) were added into a reaction flask. The reaction mixture was heated to 60° C. and reacted under stirring for 6 h. The reaction mixture was cooled to room temperature, added with p-toluenesulfonic acid monohydrate (3.65 g, 0.0192 mol) and reacted under stirring at room temperature for 5 h. Then the reaction mixture was neutralized with saturated sodium bicarbonate solution and subjected to extraction with ethyl acetate (200 mL). An organic phase was separated and then vacuum concentrated to obtain the compound (I) (38.1 g, 93% yield).

Example 27 Preparation of tert-butyl 2-[(4R,6S)-6-[(benzo[d]thiazol-2-ylthio)methyl]-2,2-disubstituted-1,3-dioxan-4-yl)] acetate (I)

Tert-butyl 2-[(4R,6S)-6-bromomethyl-2-oxo-1,3-dioxan-4-yl)] acetate (30.9 g, 0.1 mol), 2-mercaptobenzothiazole (18.4 g, 0.11 mol), potassium carbonate (15.2 g, 0.11 mol) and butanone (150 mL) were added into a reaction flask. The reaction mixture was heated to 60° C. reacted under stirring for 6 h. The reaction mixture was cooled to room temperature, added with p-toluenesulfonic acid monohydrate (3.65 g, 0.0192 mol) and reacted under stirring at room temperature for 6 h. Then the reaction mixture was neutralized with saturated sodium bicarbonate solution and subjected to extraction with ethyl acetate (200 mL). An organic phase was separated and then vacuum concentrated to obtain the compound (I) (39.61 g, 93.5% yield).

Example 28 Preparation of tert-butyl 2-[(4R,6S)-6-[(benzo[d]thiazol-2-ylthio)methyl]-2,2-disubstituted-1,3-dioxan-4-yl)] acetate (I)

Tert-butyl 2-[(4R,6S)-6-bromomethyl-2-oxo-1,3-dioxan-4-yl)] acetate (30.9 g, 0.1 mol), 2-mercaptobenzothiazole (18.4 g, 0.11 mol), potassium carbonate (15.2 g, 0.11 mol) and methyl propyl ketone (150 mL) were added into a reaction flask. The reaction mixture was heated to 60° C. and reacted under stirring for 6 h. The reaction mixture was cooled to room temperature, added with p-toluenesulfonic acid monohydrate (3.65 g, 0.0192 mol) and reacted under stirring at room temperature for 7 h. Then the reaction mixture was neutralized with saturated sodium bicarbonate solution and subjected to extraction with ethyl acetate (200 mL). An organic phase was and then vacuum concentrated to obtain the compound (I) (41.05 g, 93.8% yield).

Example 29 Preparation of tert-butyl 2-[(4R,6S)-6-[(benzo[d]thiazol-2-ylthio)methyl]-2,2-disubstituted-1,3-dioxan-4-yl)] acetate (I)

Tert-butyl 2-[(4R,6S)-6-bromomethyl-2-oxo-1,3-dioxan-4-yl)] acetate (30.9 g, 0.1 mol), 2-mercaptobenzothiazole (18.4 g, 0.11 mol), potassium carbonate (15.2 g, 0.11 mol) and cyclohexanone (150 mL) were added into a reaction flask. The reaction mixture was heated to 60° C. and reacted under stirring for 6 h. The reaction mixture was cooled to room temperature, added with p-toluenesulfonic acid monohydrate (3.65 g, 0.0192 mol) and reacted under stirring at room temperature for 5 h. Then the reaction mixture was neutralized with saturated sodium bicarbonate solution and subjected to extraction with ethyl acetate (200 mL). An organic phase was separated and then vacuum concentrated to obtain the yellowish-brown compound (I) (41.86 g, 93.1% yield).

Example 30 Preparation of tert-butyl 2-[(4R,6S)-6-[(benzo[d]thiazol-2-ylthio)methyl]-2,2-disubstituted-1,3-dioxan-4-yl)] acetate (I)

Tert-butyl 2-[(4R,6S)-6-bromomethyl-2-oxo-1,3-dioxan-4-yl)] acetate (30.9 g, 0.1 mol), 2-mercaptobenzothiazole (18.4 g, 0.11 mol), potassium carbonate (15.2 g, 0.11 mol) and 2-methylcyclohexanone (150 mL) were added into a reaction flask. The reaction mixture was heated to 60° C. and reacted under stirring for 6 h. The reaction mixture was cooled to room temperature, added with p-toluenesulfonic acid monohydrate (3.65 g, 0.0192 mol) and reacted under stirring at room temperature for 5 h. Then the reaction mixture was neutralized with saturated sodium bicarbonate solution and subjected to extraction with ethyl acetate (200 mL). An organic phase was separated and then vacuum concentrated to obtain the compound (I) (42.89 g, 92.5% yield).

Example 31 Preparation of tert-butyl 2-[(4R,6S)-6-[(benzo[d]thiazol-2-ylthio)methyl]-2,2-disubstituted-1,3-dioxan-4-yl)] acetate (I)

Tert-butyl 2-[(4R,6S)-6-bromomethyl-2-oxo-1,3-dioxan-4-yl)] acetate (30.9 g, 0.1 mol), 2-mercaptobenzothiazole (18.4 g, 0.11 mol), potassium carbonate (15.2 g, 0.11 mol) and benzophenone (150 mL) were added into a reaction flask. The reaction mixture was heated to 60° C. and reacted under stirring for 6 h. The reaction mixture was cooled to room temperature, added with p-toluenesulfonic acid monohydrate (3.65 g, 0.0192 mol) and reacted under stirring at room temperature for 4 h. Then the reaction mixture was neutralized with saturated sodium bicarbonate solution and subjected to extraction with ethyl acetate (200 mL). An organic phase was separated and then vacuum concentrated to obtain the compound (I) (49.15 g, 92.1% yield).

Example 32 Preparation of tert-butyl 2-[(4R,6S)-6-[(benzo[d]thiazol-2-ylthio)methyl]-2,2-disubstituted-1,3-dioxan-4-yl)] acetate (I)

Tert-butyl 2-[(4R,6S)-6-bromomethyl-2-oxo-1,3-dioxan-4-yl)] acetate (30.9 g, 0.1 mol), 2-mercaptobenzothiazole (18.4 g, 0.11 mol), potassium carbonate (15.2 g, 0.11 mol) and 4-methylbenzophenone (150 mL) were added into a reaction flask. The reaction mixture was heated to 60° C. and reacted under stirring for 6 h. The reaction mixture was cooled to room temperature, added with p-toluenesulfonic acid monohydrate (3.65 g, 0.0192 mol) and reacted under stirring at room temperature for 5 h. Then the reaction mixture was neutralized with saturated sodium bicarbonate solution and subjected to extraction with ethyl acetate (200 mL). An organic phase was separated and then vacuum concentrated to obtain the compound (I) (50.28 g, 91.8% yield).

Example 33 Preparation of tert-butyl 2-[(4R,6S)-6-[(benzo[d]thiazol-2-ylthio)methyl]-2,2-disubstituted-1,3-dioxan-4-yl)] acetate (I)

Tert-butyl 2-[(4R,6S)-6-bromomethyl-2-oxo-1,3-dioxan-4-yl)] acetate (30.9 g, 0.1 mol), 2-mercaptobenzothiazole (18.4 g, 0.11 mol), potassium carbonate (15.2 g, 0.11 mol) and phenylacetone (150 mL) were added into a reaction flask. The reaction mixture was heated to 60° C. and reacted under stirring for 6 h. The reaction mixture was cooled to room temperature, added with p-toluenesulfonic acid monohydrate (3.65 g, 0.0192 mol) and reacted under stirring at room temperature for 5 h. Then the reaction mixture was neutralized with saturated sodium bicarbonate solution and subjected to extraction with ethyl acetate (200 mL). An organic phase was separated and then vacuum concentrated to obtain the compound (I) (45.36 g, 93.4% yield).

Example 34 Preparation of tert-butyl 2-[(4R,6S)-6-[(benzo[d]thiazol-2-ylthio)methyl]-2,2-disubstituted-1,3-dioxan-4-yl)] acetate (I)

Tert-butyl 2-[(4R,6S)-6-bromomethyl-2-oxo-1,3-dioxan-4-yl)] acetate (30.9 g, 0.1 mol), 2-mercaptobenzothiazole (18.4 g, 0.11 mol), potassium carbonate (15.2 g, 0.11 mol) and 4-methyl-1-phenyl-2-pentanone (150 mL) were added into a reaction flask. The reaction mixture was heated to 60° C. and reacted under stirring for 6 h. The reaction mixture was cooled to room temperature, added with p-toluenesulfonic acid monohydrate (3.65 g, 0.0192 mol) and reacted under stirring at room temperature for 5 h. Then the reaction mixture was neutralized with saturated sodium bicarbonate solution and subjected to extraction with ethyl acetate (200 mL). An organic phase was separated and then vacuum concentrated to obtain the compound (I) (48.6 g, 92.1% yield).

Example 35 Preparation of tert-butyl 2-[(4R,6S)-6-[(benzo[d]thiazol-2-ylthio)methyl]-2,2-disubstituted-1,3-dioxan-4-yl)] acetate (I)

Tert-butyl 2-[(4R,6S)-6-bromomethyl-2-oxo-1,3-dioxan-4-yl)] acetate (30.9 g, 0.1 mol), 2-mercaptobenzothiazole (18.4 g, 0.11 mol), potassium carbonate (15.2 g, 0.11 mol) and cyclopropyl methyl ketone (150 mL) were added into a reaction flask. The reaction mixture was heated to 60° C. and reacted under stirring for 6 h. The reaction mixture was cooled to room temperature, added with p-toluenesulfonic acid monohydrate (3.65 g, 0.0192 mol) and reacted under stirring at room temperature for 5 h. Then the reaction mixture was neutralized with saturated sodium bicarbonate solution and subjected to extraction with ethyl acetate (200 mL). An organic phase was separated and then vacuum concentrated to obtain the compound (I) (40.21 g, 92.3% yield).

It should be noted that the embodiments provided herein are merely illustrative, and are not intended to limit the invention. Any change, modification and replacement made by those skilled in the art without departing from the spirit of the invention should fall within the scope of the invention defined by the appended claims.

What is claimed is:
1. A method for preparing 2-[(4R,6S)-6-[(benzo[d]thiazol-2-ylthio)methyl]-2,2-disubstituted-1,3-dioxan-4-yl] acetate of formula (I):

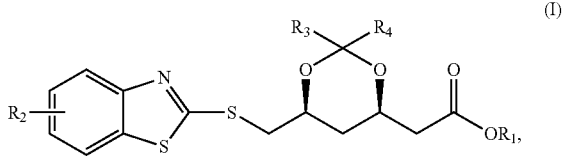

wherein $R_1$ is a $C_1$-$C_8$ alkyl group, a $C_3$-$C_8$ cycloalkyl group, a $C_6$-$C_{10}$ aryl group, or a $C_7$-$C_{12}$ aralkyl group; $R_2$ is hydrogen, a $C_1$-$C_3$ alkyl group, or halogen; and $R_3$ and $R_4$ are each independently a $C_1$-$C_5$ alkyl group, a $C_3$-$C_7$ cycloalkyl group, a $C_3$-$C_7$ cycloalkenyl group, a $C_1$-$C_3$ alkoxy group, a $C_6$-$C_{10}$ aryl group, or a $C_7$-$C_{12}$ aralkyl group;

wherein the method comprising:
(1) subjecting 2-[(4R,6S)-6-halomethyl-2-oxo-1,3-dioxan-4-yl] acetate (II) and a 2-mercaptobenzothiazole compound (III) to nucleophilic substitution in an organic solvent to synthesize 2-[(4R,6S)-6-[(benzo[d]thiazol-2-ylthio)methyl]-2-oxo-1,3-dioxan-4-yl] acetate (IV),

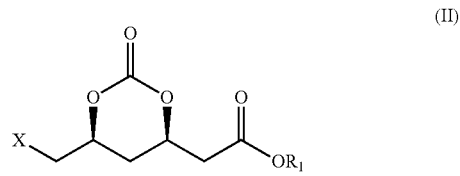

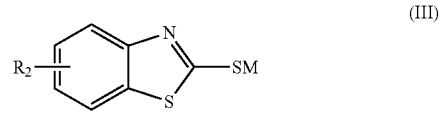

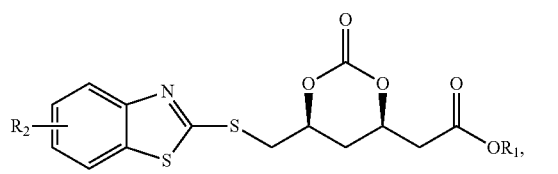

wherein X is halogen; and M is hydrogen, alkali metal cation, ammonium ion or phosphonium ion; and
wherein the organic solvent is selected from the group consisting of N,N-dimethylformamide, dimethyl sulfoxide, N-methylpyrrolidone, sulfolane, 1,3-dimethyl-2-imidazolidinone, hexamethylphosphoric triamide, acetonitrile, a ketone solvent, N-alkylpyridinium salt, 1,3-dialkyl imidazolium salt and a combination thereof; and (2) subjecting 2-[(4R,6S)-6-[(benzo[d]thiazol-2-ylthio)methyl]-2-oxo-1,3-dioxan-4-yl]acetate (IV) and a carbonyl compound (V) to ketal exchange reaction in the presence of an organic acid to synthesize the 2-[(4R,6S)-6-[(benzo[d]thiazol-2-ylthio)methyl]-2,2-disubstituted-1,3-dioxan-4-yl] acetate (I),

(V)

2. The method of claim 1, wherein 2-mercaptobenzothiazole compound (III) is 2-mercaptobenzothiazole;
the step (1) specifically comprises:
subjecting 2-[(4R,6S)-6-halomethyl-2-oxo-1,3-dioxan-4-yl] acetate (II) and 2-mercaptobenzothiazole to nucleophilic substitution in the organic solvent in the presence of a base to synthesize 2-[(4R,6S)-6-[(benzo[d]thiazol-2-ylthio)methyl]-2-oxo-1,3-dioxan-4-yl] acetate (IV);
wherein the base is an inorganic base or an organic base; the inorganic base is alkali metal carbonate, alkali metal bicarbonate, alkali metal hydroxide or a combination thereof; and the organic base is sodium methoxide, sodium ethoxide, sodium tert-butoxide, potassium tert-butoxide, triethylamine, pyridine or a combination thereof.

3. The method of claim 1, wherein when the M in the formula (III) is hydrogen, the nucleophilic substitution in step (1) is performed in the presence of a base; the base in step (1) is an inorganic base; the inorganic base such is lithium carbonate, sodium carbonate, potassium carbonate, cesium carbonate, lithium bicarbonate, sodium bicarbonate, potassium bicarbonate, lithium hydroxide, sodium hydroxide or potassium hydroxide; or
when the 2 mercaptobenzothiazole compound (III) is a 2-mercaptobenzothiazole salt, the nucleophilic substitution in step (1) is performed in the absence of the base.

4. The method of claim 1, wherein the ketone solvent is selected from the group consisting of symmetric alkyl ketone, symmetric cycloalkyl ketone, asymmetric alkyl ketone, asymmetric cycloalkyl ketone, symmetric aryl ketone, symmetric aralkyl ketone, asymmetric aryl ketone, asymmetric aralkyl ketone and a combination thereof.

5. The method of claim 1, wherein in step (1), a concentration of 2-[(4R,6S)-6-halomethyl-2-oxo-1,3-dioxan-4-yl] acetate (II) is 0.1-5 mol/L.

6. The method of claim 1, wherein in step (1), a molar ratio of 2 [(4R,6S)-6-halomethyl-2-oxo-1,3-dioxan-4-yl] acetate (II) to 2 mercaptobenzothiazole compound (III) is 1:0.5-5.

7. The method of claim 6, wherein in step (1), the molar ratio of 2 [(4R,6S)-6-halomethyl-2-oxo-1,3-dioxan-4-yl] acetate (II) to 2 mercaptobenzothiazole compound (III) is 1:1-3.

8. The method of claim 1, wherein in step (1), the nucleophilic substitution is performed at 20-180° C. for 1-18 h.

9. The method of claim 8, wherein in step (1), the nucleophilic substitution is performed at 30-90° C. for 4-10 h.

10. The method of claim 1, wherein in step (2), the organic acid is p-toluenesulfonic acid, methanesulfonic acid, benzenesulfonic acid or camphor sulfonic acid.

11. The method of claim 10, wherein in step (2), the organic acid is p-toluenesulfonic acid or benzenesulfonic acid.

12. The method of claim 1, wherein in step (2), a concentration of 2-[(4R,6S)-6-[(benzo[d]thiazol-2-ylthio)methyl]-2-oxo-1,3-dioxan-4-yl] acetate (IV) is 0.1-5 mol/L.

13. The method of claim 1, wherein in step (2), a molar ratio of 2-[(4R,6S)-6-[(benzo[d]thiazol-2-ylthio)methyl]-2-oxo-1,3-dioxan-4-yl] acetate (IV) to the organic acid is 1:0.01-5.

14. The method of claim 13, wherein in step (2), the molar ratio of 2-[(4R,6S)-6-[(benzo[d]thiazol-2-ylthio)methyl]-2-oxo-1,3-dioxan-4-yl] acetate (IV) to the organic acid is 1:0.1-1.

15. The method of claim 1, wherein in step (2), the ketal exchange reaction is performed at 10-80° C. for 1-48 h.

16. The method of claim 15, wherein the ketal exchange reaction in step (2) is performed at 15-50° C. for 3-10 h.

* * * * *